United States Patent [19]

Cohen-Tenoudji et al.

[11] Patent Number: 4,779,452
[45] Date of Patent: Oct. 25, 1988

[54] HIGH TEMPERATURE ULTRASONIC VISCOMETER

[75] Inventors: Frederic Cohen-Tenoudji, Neuilly, France; Lloyd A. Ahlberg, deceased, late of Thousand Oaks, Calif., by Margaret L. Ahlberg, heir; Bernhard R. Tittmann, Thousand Oaks; William J. Pardee, Newbury Park, both of Calif.

[73] Assignee: Rockwell International Corporation, El Segundo, Calif.

[21] Appl. No.: 872,315

[22] Filed: Jun. 9, 1986

[51] Int. Cl.⁴ .................................................. G01N 11/00
[52] U.S. Cl. ................................................................ 73/54
[58] Field of Search ............................. 73/54, 690, 692

[56]   References Cited
   U.S. PATENT DOCUMENTS 2,755,662  7/1956  Swengel ................................. 73/54
   3,553,636  1/1971  Baird ...................................... 73/54
   4,559,810 12/1985  Hinrichs et al. ....................... 73/54

*Primary Examiner*—Stewart J. Levy
*Assistant Examiner*—Hezron E. Williams
*Attorney, Agent, or Firm*—H. Fredrick Hamann; Craig O. Malin; Max Geldin

[57]   ABSTRACT

An ultrasonic viscometer is described which is particularly designed for monitoring the viscosity of a thermally curing resin or composite, such as a fiber-reinforced epoxy composite, in an autoclave at high temperature. According to a preferred embodiment, the viscometer comprises a piezoelectric element of lithium niobate crystals bonded to a first buffer of copper, which is bonded on the other side to a second buffer of aluminum. The resin or composite is in contact with the second buffer. When the transducer emits a short ultrasonic pulse, two echoes are reflected back, the first echo being generated by the copper-aluminum interface, the second by the aluminum-resin interface. The signals from the two echoes are processed to obtain the complex reflection coefficient at the interface of the second buffer and the resin, from which the viscosity of the resin can be calculated and the cure state of the resin determined.

17 Claims, 4 Drawing Sheets

HIGH TEMPERATURE ULTRASONIC VISCOMETER

BACKGROUND OF THE INVENTION

This invention relates generally to the field of viscosity control technology and is particularly directed to an ultrasonic viscometer device to measure the viscosity and the cure state of a thermally curing polymer composite at high temperature using the reflectivity of ultrasonic shear waves. Such viscosity measurement permits the control and the optimization of the cure cycle to minimize porosity and delaminations in the composite.

Fiber-reinforced composite materials, known as "composites", comprise a base or substrate material, such as an epoxy resin, which is impregnated, for structural strength, with fibers of such materials as carbon, graphite, glass, boron and nylon. Composites typically exhibit extremely high strength-to-weight ratios, and accordingly, their use is becoming increasingly important in commercial and aerospace applications.

Such composite materials, as previously noted, are typically based upon a matrix of thermo-curing polymers or resins, such as epoxies, which are usually cured at high temperatures in an autoclave. Under the effect of increasing temperature, the polymer molecules grow into longer chains and branches. In the case of thermosetting polymers, crosslinks between the chains are also formed. The rate of the reaction is a complex function of the temperature and pressure which depends upon the thickness and geometry of the part being made, on the thermal equilibrium between the part and the mold, on the temperature of the atmosphere around the part and/or the thermal mass of the autoclave. The monitoring of the viscoelastic properties of the resin provide important information on the state of the cure and allow the control of the flow properties. Molding operations may be optimized and the content of voids minimized by a better control of the degree of resin compaction.

Although mechanical measurement of viscosity can be made, this requires the insertion of a probe into the composite part being cured. This operation generally is not feasible during manufacture of a composite part and, particularly, when several determinations of viscosity are necessary from different locations on the part.

Some chemical techniques have been developed to monitor the cure state of a resin but are difficult to implement in a manufacturing environment. Some examples are high-performance liquid chromatography, differential scanning calorimetry, which determines the state of the cure by the heat generation needed to complete the cure, and infrared spectroscopy.

Ultrasonic methods have been used for some time to measure resin viscosity and the cure state thereof. An advantage of ultrasonic wave propagation for measuring the viscosity of a medium, such as a resin during cure thereof, is that it depends directly on the mechanical constants of the medium of propagation. In principle, ultrasonic techniques then provide a way to measure these constants. However, the mechanical constants vary significantly with frequency, sometimes by several orders of magnitude between the range of a few Hertz, where they are a function of the flow properties of the resin, and the MegaHertz range where ultrasonic techniques have been used more often.

Thus, the article, "Dynamic Viscoelastic Properties of Cholesteric Liquid Crystals", by J. F. Dyro, et al, MOL Cryst. & Liq. Cryst., Vol. 29, No. 3-4, 263-84, 1975, discloses use of reflectivity of shear waves to obtain the dynamic shear viscosity of cholesteric liquid crystals from 35° to 55° C. However, this procedure would appear to require a thermal equilibrium bath and could not be performed in an autoclave.

The article, "Ultrasonic Viscometer for the Measurement of Dynamic Shear Viscosity of Liquids", V. N. Bindal, et al, Indian J. Pure Appl. Phys., Vol. 21, No. 3, March, 1983, pp. 176-177, discloses an ultrasonic viscometer for the measurement of dynamic shear viscosity of liquids using a quartz crystal along with a fused quartz delay line. Apparently, the temperatures reached are below 100° C., and the system apparently operates under temperature control, that is, stabilized temperature, conditions. However, the use of such technique in an autoclave with a quickly varying temperature would not be feasible.

The use of ultrasound to monitor the cure of epoxies has been proposed. The technique most commonly used for this purpose has been the measurement of velocity and attenuation of longitudinal and shear waves.

U.S. Pat. No. 4,559,810 to Hinrichs, et al, discloses a method for determining the dynamic viscosity of a specimen of a polymeric resin which is subjected to a time-varying temperature by passing an ultrasonic sensing wave of known amplitude through the specimen, sensing the amplitude of the wave after it has traveled through the specimen, and from the degree of amplitude attenuation, obtaining a value which has a linear relationship to the logarithm of the dynamic viscosity of the resin.

SUMMARY OF THE INVENTION

It is an object of the invention to provide an improved ultrasonic viscometer for measuring the viscosity of a liquid medium, particularly at elevated temperature.

Another object of the invention is the provision of a high temperature ultrasonic viscometer employing shear waves to monitor the viscosity characteristics of a thermally curing resin, such as an epoxy resin.

A still further object is to provide a high temperature ultrasonic viscometer to measure the cure state of a thermally curing polymer composite, such as a fiber-reinforced epoxy composite, in an autoclave, at high temperatures, using the reflectivity of ultrasonic shear waves, without cooling the transducer.

According to the invention, there is provided an ultrasonic viscometer, particularly designed for monitoring the viscosity of a thermally curing resin, from the reflection coefficient of shear waves. The waves are generated by a piezoelectric element bonded to a first buffer. A second buffer is bonded to the first, and the subject liquid medium, such as a resin, is in contact with the second buffer. A first echo generated at the interface of the two buffers is used for normalization. The second echo is generated at the interface of the second buffer with the liquid medium or resin. The signals from the two echoes are processed to obtain the complex reflection coefficient at the interface of the second buffer and the medium or resin, from which the viscosity of the medium can be calculated and the cure state of the resin determined.

In the operation of the above system, the first echo is formed by shear waves generated by the piezoelectric element which are partially reflected at the first interface of the two buffers, and the second echo is formed by waves transmitted across such interface and reflected at the second interface of the second buffer and the medium or resin whose viscosity is being measured. The buffers are comprised of materials having different acoustic impedance, the echo generated at their interface being utilized as a reference. The thickness of the second buffer is sufficient to allow the differentiation in time of the two signals.

According to a preferred embodiment, the piezoelectric element, comprised of lithium niobate crystals, is bonded to a first buffer of copper, which is bonded on the other side to a second buffer of aluminum. When the transducer emits a short ultrasonic pulse, two echoes are reflected back, the first echo being generated by the copper-aluminum interface, the second by the aluminum-resin interface or, in the absence of a resin, by the aluminum-air interface. This latter signal is used for calibration and for correction of thermal fluctuation effects.

The invention thus provides an ultrasonic viscometer having a unique transducer-buffer assembly that operates at high temperature and can be incorporated directly into an autoclave in contact with a composite during curing, enabling determination of the state of the cure to control the cure cycle and obtain cured composite components of good mechanical characteristics and low porosity.

BRIEF DESCRIPTION OF THE DRAWINGS

The invention will be more clearly understood by reference to the preferred embodiment set forth hereinafter, taken in conjunction with the accompanying drawings, wherein.

DESCRIPTION OF THE PREFERRED EMBODIMENT

According to the invention, a transducer-buffer assembly is provided which permits the accurate measurement of the reflection coefficient of ultrasonic shear waves at the tool-resin interface at temperatures up to 190° C. In the invention system, signal processing techniques are used to correct for thermal fluctuation effects and to extract the elastic (real) and the viscous (imaginary) components of the shear modulus of the subject medium or resin whose viscosity is being measured. The dynamic viscosity in the MHz range is then calculated from the imaginary or viscous component of the shear modulus.

Figure 1:
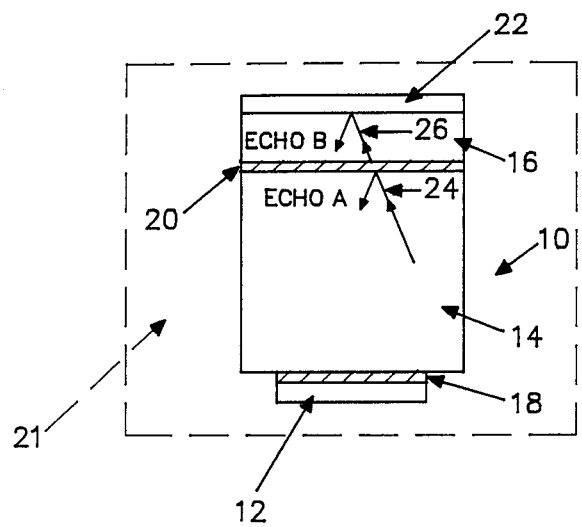
FIG. 1 is an illustration of a preferred form of ultrasonic viscometer according to the invention, comprised of an aluminum-copper buffer system.

Referring to FIG. 1 of the drawing, the ultrasonic viscometer 10 consists of a transducer buffer assembly essentially comprised of three parts, a piezoelectric element 12, a first buffer rod 14 and a second buffer rod 16. The piezoelectric element 12 is bonded to the first buffer rod 14 and the second buffer rod 16 is bonded to the first buffer rod 14.

The piezoelectric element generates acoustic shear waves and is capable of sustaining high temperatures without depolarization or cracking. Lithium niobate crystals are particularly preferred. The piezoelectric element can be comprised of other materials including the material marketed as C5500 ceramic by Channel Industries, understood to be a lead zirconate-lead titanate composition. Another suitable composition is lead metaniobate. The conventional quartz piezoelectric element also can be employed. However, it has the disadvantage that it resonates longer, and does not generate a very short pulse, which is advantageous. Quartz also does not have the efficiency of transduction from voltage to ultrasound as does lithium niobate or the above-described C5500 material.

The piezoelectric element 12, e.g., lithium niobate transducer, is gold-plated so that a clean electric field can be set up across the piezoelectric element. However, it is not essential to gold-plate the piezoelectric element.

The first buffer rod 14 to which the transducer 12 is bonded can be, for example, several centimeters, e.g., 3.0 cm., long. Such first buffer can be comprised of different materials. Such first buffer should be composed of a material having good thermal conductivity to insure that there is no temperature gradient inside the buffer. A preferred first buffer material is copper, with alternative materials being silver or gold.

In order to achieve a reliable bond at high temperature, the transducer or piezoelectric element 12 is welded at 18 to the first buffer rod 14. A preferred solder or welding material for this purpose is a tin-silver solder with a melting temperature of 221° C. Other solder alloys, such as lead-tin-silver, having a melting temperature of about 190° C. can be employed, as well as higher melting solders.

The second buffer rod 16 is shorter than the first buffer rod 14, for example, about one centimeter long. The second buffer rod has a low shear wave acoustic impedance for better sensitivity. It is desirable that the acoustic impedance of the second buffer rod be as low as possible to match that of the resin, e.g., the epoxy resin in a graphite-epoxy composite material. The second buffer rod 16 is preferably comprised of aluminum. However, buffer rod 16 can be comprised of other materials, such as magnesium, which has the disadvantage that it will burn at high temperature. Quartz or fused silica also can be used for the second buffer rod 16, but this material is not a good thermal conductor and is difficult to bond to the first buffer rod 14.

The preferred aluminum second buffer rod 16 is electroplated with another metal in order to weld the aluminum buffer successfully to the copper buffer rod 14, since aluminum cannot be soldered due to rapid oxidation thereof. The second buffer rod 16 accordingly is electroplated with copper for most efficient welding of the aluminum buffer rod 16 to the copper buffer rod 14. Alternatively, the aluminum buffer rod 16 can be gold-plated for soldering to the copper buffer rod 14.

The copper-plated aluminum buffer rod 16 is preferably welded to the copper buffer rod 14 using the same solder alloy as employed in welding the transducer 12 to the first buffer rod 14. Thus, the second buffer rod 16 can be welded to the first buffer rod 14 using the same tin-silver alloy solder at 20, employed at 18 for welding the transducer 12 to the first buffer rod 14. The welding of the second buffer rod 16 to the first buffer rod 14 can be carried out at the same time as the transducer 12 is welded to the first buffer rod 14.

Alternatively, the second aluminum buffer rod 16 can be bonded to the first copper buffer rod 14 by the technique of diffusion bonding. Such diffusion bonding is carried out at elevated temperature in the range between about 400° C. and 1100° C. to establish a series of Cu-Al phases between 100% Cu and 100% Al. This procedure is based on information contained in Hansen's "Constitution of Binary Alloys", McGraw-Hill (1958), pp. 84–86.

In operation, where the ultrasonic viscometer is employed to monitor the viscosity of a composite, such as a graphite-epoxy composite during high temperature curing, the ultrasonic viscometer 10 is placed in an autoclave indicated at 21, in which the composite is cured, with the end of the aluminum buffer rod 16 in contact with the graphite-epoxy composite, indicated at 22.

Figure 2:
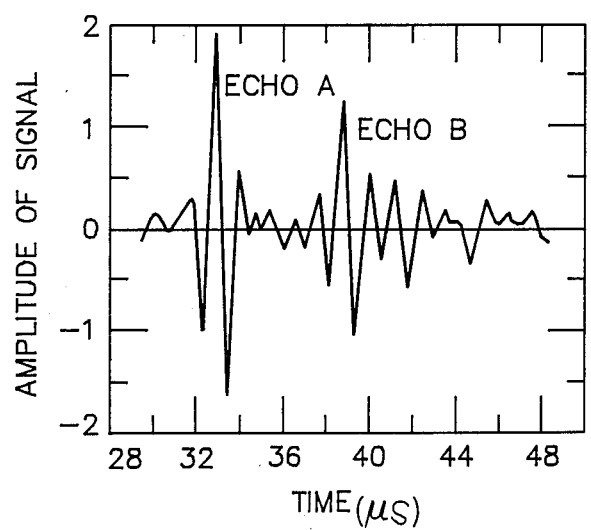
FIG. 2 illustrates reflected signals from the copper-aluminum interface and from the aluminum-third medium interface.

An alternating current voltage field is set up for a very short period of time between the bottom and top gold film on each side of the piezoelectric element 12, to excite the element. The piezoelectric element thus generates ultrasonic shear waves which first pass through the first buffer rod 14 and are partially reflected at the copper-aluminum interface, as indicated by the arrow 24, to form a first echo A. The first echo A is used as a reference for calibration and for correction of thermal fluctuation effects. The shear waves transmitted across the Cu-Al interface pass through the aluminum buffer rod 16, as indicated by arrow 26, and are reflected at the second interface between the aluminum buffer rod 16 and the epoxy composite 22 to form a second echo B. Examples of signals generated by echoes A and B in the time domain are illustrated in FIG. 2, showing the amplitude of the signals versus time.

The signals from the echoes A and B are digitized and processed in a computer. The complex reflection coefficient (magnitude and phase) at the aluminum-epoxy composite interface is obtained, from which the elasticity and the viscosity of the resin of the composite are calculated.

If desired, the ultrasonic transducer 10 can be operated first in the absence of the resin or composite 22 so that the second echo B is provided by the aluminum-air interface. This latter signal is used for normalization. However, such normalization or separate calibration with air is not necessary since all of the calibration required can be obtained in the process using only the aluminum-resin interface.

The term "buffer" in the above-noted expression "buffer rod" is intended to denote a "delay line", which provides an acoustic travel time. Thus, the ultrasonic pulse first travels to the interface between the aluminum and the copper, and at that point, due to the acoustic impedance mismatch between the copper and the aluminum, some of the signal is returned back at that point, and the remainder of the energy travels on to the aluminum-resin interface, and another pulse comes back. The term "buffer" is used to describe the process of separating these two pulses, in the nature of a delay line or a delay system that allows separation of the two pulses.

The thickness of the second aluminum buffer 16 is the minimum possible, e.g., about 1 centimeter in a preferred embodiment, in order to minimize the errors induced by the temperature variations, but is still large enough to allow the differentiation in time of the two signals.

It has been found that in order to obtain reliable results, the bonds between the transducer element 12 and the first buffer 14, and between the two buffers 14 and 16, must be very stable mechanically. Since the system must be used over a large temperature range, the bonds must be able to sustain the high shear stresses resulting from the different thermal expansions between the transducer and the first buffer 14 and between the two buffers 14 and 16.

Figure 3:
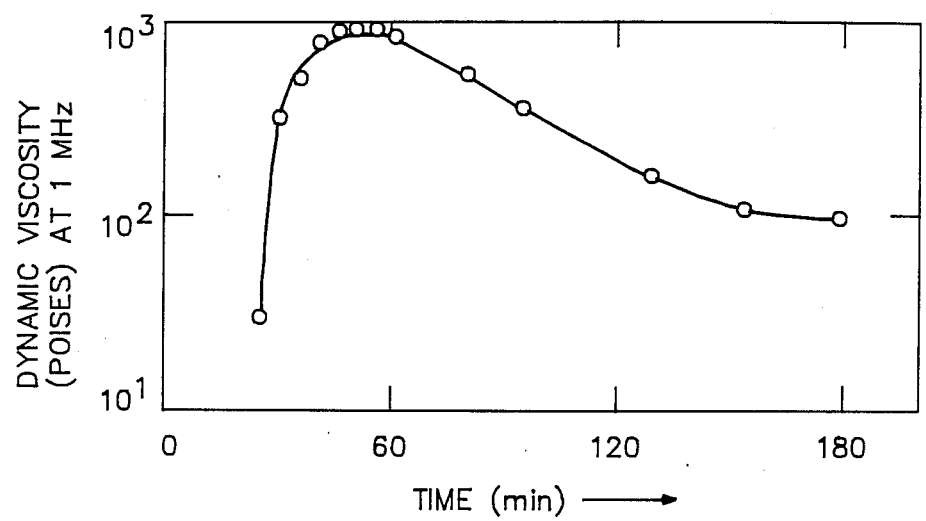
FIG. 3 is a graph illustrating measured viscosity of an epoxy resin at various stages during cure thereof.

In an example of operation, the ultrasonic viscometer 10 of FIG. 1 was employed to monitor the viscosity of the thermally curing epoxy Hercules 3501 resin. The curing took place over a temperature ranging from 25° C. to 121° C. at a rate of 4° C. per minute. The ultrasonic viscometer was operated to produce ultrasound at 1 MHz. The viscosity variations for the thermally curing resin during the cure cycle are shown in the plot of FIG. 3 of viscosity in poises versus time.

FIGS. 4–6b of the drawings establish the relationship between the dynamic viscosity and the degree of cure of the above epoxy resin.

Figure 4:
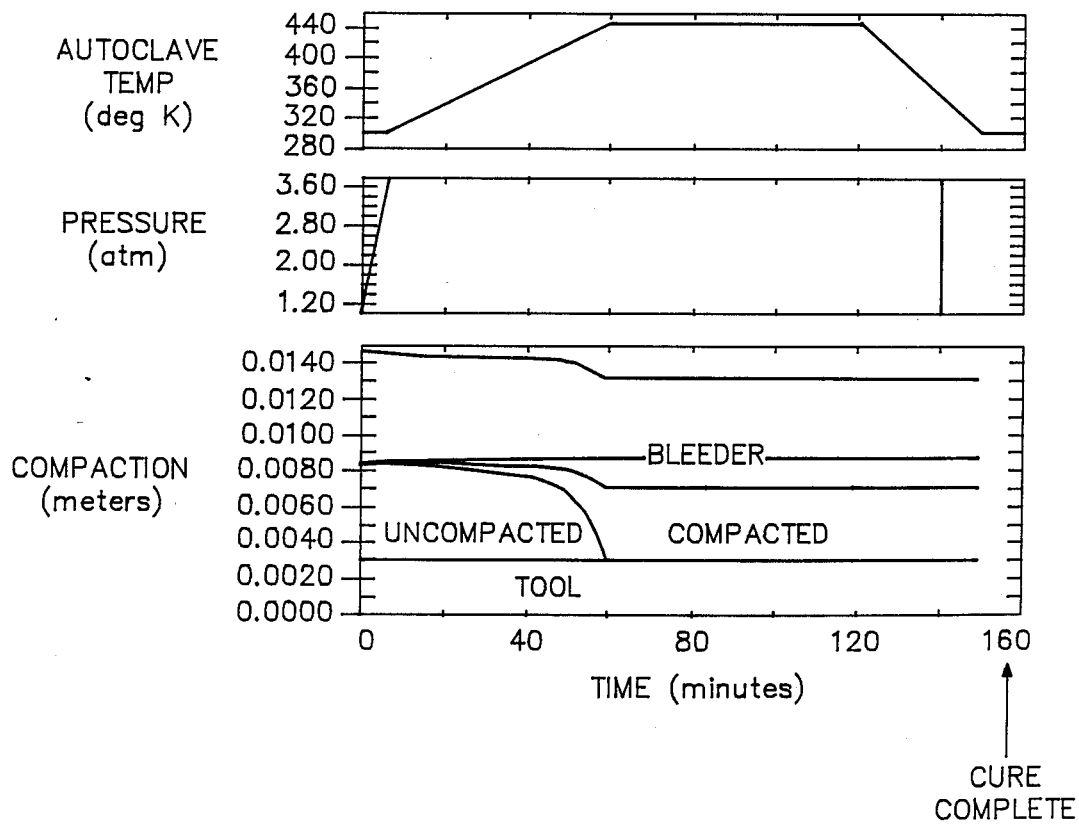
FIGS. 4, 5, 6a and 6b illustrate the relation between viscosity and degree of cure of such epoxy resin.

FIG. 4 shows the autoclave temperature, pressure and the compaction as a function of time into the cure operation. It is seen from FIG. 4 that the cure is completed after 160 minutes.

Figure 5:
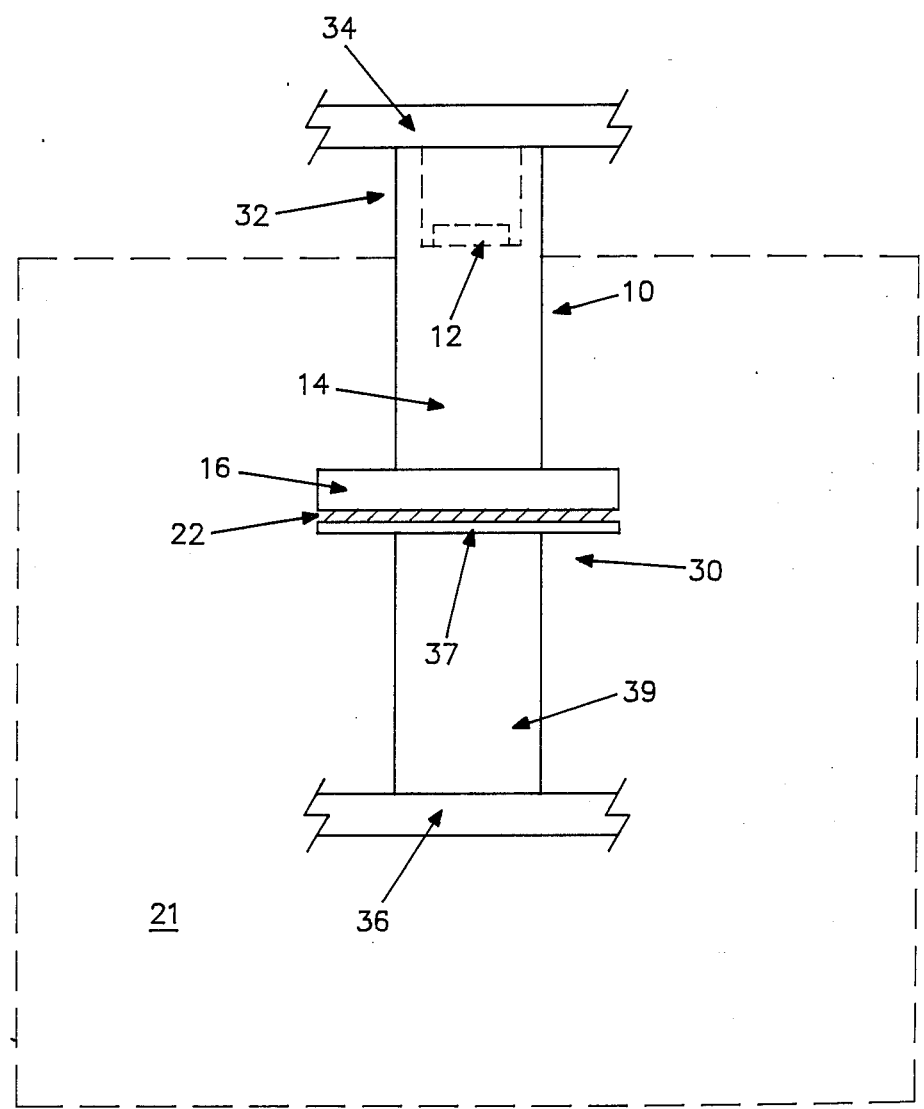

For non-fiber filled resins, one is able to follow rhe cure cycle with a modified rheometer shown in FIG. 5. In this figure, a rheometer, indicated at 30, has been modified to incorporate an ultrasonic viscometer according to the invention to allow a measurement of the viscosity of the resin simultaneously by both the rheometer and the ultrasonic viscometer of the invention.

Thus, referring to FIG. 5, for this purpose, the rotating superior portion 32 of a torque rheometer 30 has been modified to accommodate the two-part buffer ultrasonic viscometer 10 of the invention. In this rheometer, the fluid resin sample 22 is contained between two parallel rotating disks, indicated at 34 and 36, of the rheometer. A member 37 of the torque rheometer 30 is in contact with one side of the resin sample 22, the other side of the resin sample contacting the aluminum buffer rod 16 of the ultrasonic viscometer 10. A torque transmitting pick-up member 39 is positioned between one of the disks 36 of the rheometer 30 and member 37. The shear transducer 12 of the ultrasonic viscometer is connected to the other disk 34 of the rheometer.

Due to the viscosity of the fluid resin 22, the periodic rotation of upper disk 34 induces a rotation of the other lower disk 36. The viscosity is calculated from the respective magnitudes and phases of the movements of rotation of the two disks.

In one embodiment, the shear transducer 12 of the ultrasonic viscometer 10 in the upper part measures the viscosity at 1 MHz from the reflectivity of the resin. The rotation of the upper disk 34 induces rotation of the lower one 36 through the resin at 10 Hz, from which the viscosity is determined at that frequency.

Figure 6A:
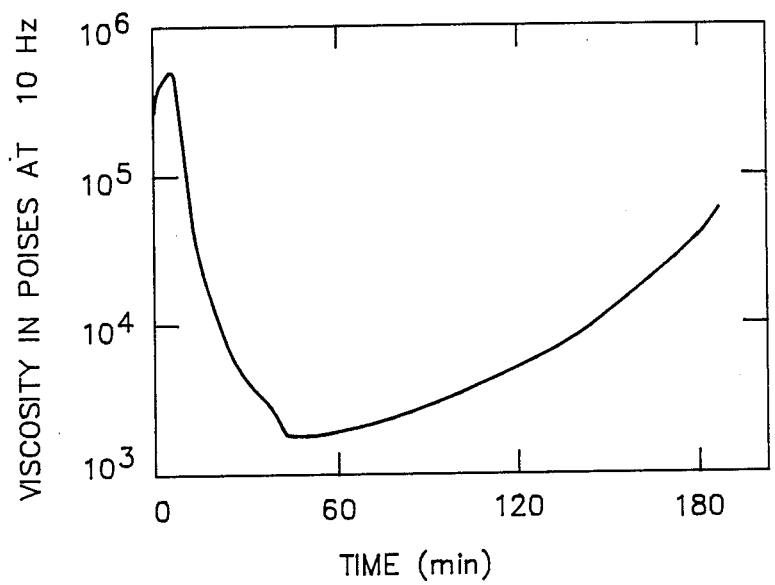
Figure 6B:
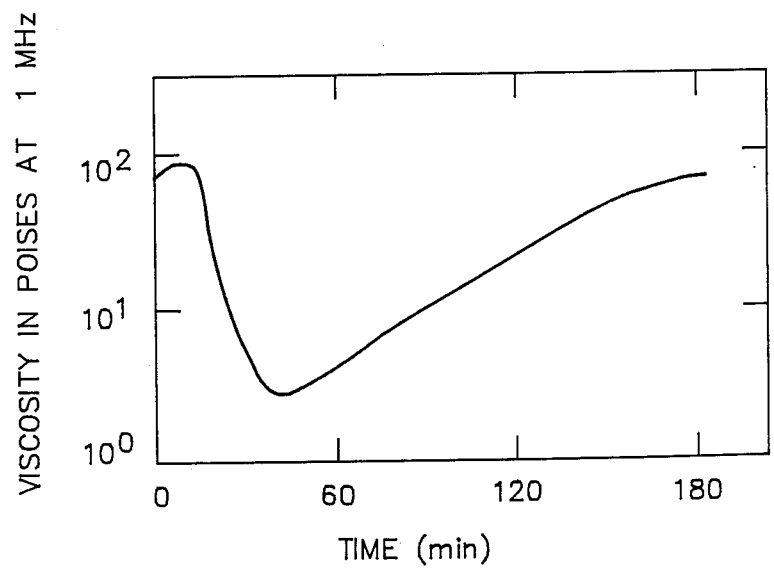

In the above-noted example of operation, employing the ultrasonic viscometer 10 to monitor the viscosity of the thermally curing epoxy Hercules 3501 resin, in conjunction with the rheometer 30, as shown in FIG. 5, the experiment was ended when the epoxy became so stiff that the torque on the measuring disks reached a maximum value allowed by the equipment. In FIG. 6a, the viscosities are plotted as measured by the torque rheometer and, in FIG. 6b, by the ultrasonic viscometer. A comparison of FIG. 6a and FIG. 6b shows such a close resemblance between the two curves that it is clearly apparent that the ultrasonic measurement can be used to monitor the complete cure of a resin.

The ultrasonic viscometer of the invention is designed particularly to measure the viscosity and the cure state of a thermally curing polymer or polymer composite at high temperature, particularly epoxy resins or fiber-epoxy composites. The viscosity and cure state at elevated temperatures of other resins, such as phenolic resins, polyamides, polyimides, and their respective composites, can be measured and monitored by the invention device. The ultrasonic viscometer hereof can also be employed to measure the viscosity of other fluids, such as ink and oil, either at ambient or elevated temperature. The invention device is particularly applicable for monitoring the viscosity and cure state of composites cured in an autoclave since the viscometer hereof can be placed in intimate contact with the composite within the autoclave.

The invention accordingly provides an improved high temperature ultrasonic viscometer comprised of a compound buffer rod using two materials with different acoustic impedance, such as copper and aluminum, bonded together, and a piezoelectric element bonded to the buffer, wherein shear waves generated by the piezoelectric element generate an echo at the interface of the two buffer materials and allow the correction of the second echo from the aluminum-resin interface for phase errors induced by the temperature variations. The shear waves complex reflection coefficient measurement gives the viscosity of a fluid or resin in contact with the buffer rod, from which the state of cure of the resin can be obtained. The piezoelectric element is operated at ultrasonic frequencies in the range from about 1 to 3 MHz. The piezoelectric eleaent is preferably welded to the buffer, as are the two materials of the buffer, to provide high mechanical stability. Evaluation of the state of cure of composites by the invention device allows the control of autoclave temperature and pressure dependence with time.

The ultrasonic viscometer of the invention permits evaluation of the shear viscosity, particularly of a heat curable resin, which is a most important material property to determine the state of cure. The operation of the invention device requires only a single-sided inspection and is a non-invasive method. The calibration of the viscometer does not depend on the particular resin but only on the temperature on the buffer rod, and no cooling of the buffer is necessary.

On the other hand, it appears that the technique of the above U.S. Pat. No. 4,559,810 to Hinrichs et al requires a flat back surface which is parallel to the front surface. This is necessary for the waves to come back to the transducer. The alternative is to have two transducers one at the front face, one at the back face which is impractical since the material such as a bleeder cloth, plastic bag, etc. make it very difficult to bond a removeable transducer on the back face. The advantage of the present invention device is that it requires access to only one side. Also, it gives the local viscosity at the surface rather than a response resulting from an integration through the entire thickness of the composite.

It will be apparent that variations and modifications of the ultrasonic viscometer of the invention can be made to obtain the invention results without departing from the invention. Accordingly, it should be understood that the form of the invention described above is illustrative and is not intended as limitative of the scope of the invention.

What is claimed is:

1. An ultrasonic viscometer which comprises:
   a piezoelectric element;
   a first buffer bonded to said piezoelectric element; and
   a second buffer bonded to said first buffer and adapted to be contacted with a medium whose viscosity is to be measured,
   whereby ultrasonic shear waves generated by said piezoelectric element generate a first echo at the interface of the two buffers and a second echo at the interface of the second buffer with said medium, permitting said echoes to be processed to obtain the complex reflection coefficient at the interface of said second buffer and said medium, from which the viscosity of said medium can be calculated.

2. The viscometer of claim 1, wherein said first echo is formed by shear waves generated by said piezoelectric element which are partially reflected at the interface of the two buffers, and said second echo is formed by shear waves transmitted across said interface and reflected at the interface of the second buffer and said medium.

3. The viscometer of claim 2, wherein said buffers further comprise material having different acoustic impedance, the echo generated at their interface being utilized as a reference.

4. The viscometer of claim 3, wherein said piezoelectric element is welded to said first buffer and said second buffer is welded to said first buffer.

5. The ultrasonic viscometer of claim 3, wherein said piezoelectric element further comprises a material selected from the group consisting of lithium niobate, lead zirconate-lead titantate, lead metaniobate, and quartz.

6. The ultrasonic viscometer of claim 3, wherein said first buffer is formed of a material having good thermal conductivity and said second buffer is formed of a material having a low shear wave acoustic impedance substantially matching that of said medium.

7. The ultrasonic viscometer of claim 3, wherein said first buffer comprises a material selected from the group consisting of copper, silver, and gold, and said second buffer further comprises a material selected from the group consisting of aluminum and magnesium.

8. The ultrasonic viscometer of claim 7, wherein said first buffer further comprises copper and said second buffer further comprises aluminum.

9. The ultrasonic viscometer of claim 8, wherein said piezoelectric element is welded to said first copper buffer with a tin-silver alloy solder.

10. The ultrasonic viscometer of claim 9, wherein said second aluminum buffer is welded to said first copper buffer with a tin-silver alloy solder.

11. The ultrasonic viscometer of claim 10, wherein said aluminum buffer is electroplated with copper.

12. The ultrasonic viscometer of claim 9, wherein said second aluminum buffer is diffusion bonded to said first copper buffer.

13. The ultrasonic viscometer of claim 3, wherein said medium further comprises a heat curable resin which is curable at temperatures up to about 190° C.

14. The ultrasonic viscometer of claim 13, wherein said heat curable resin further comprises a fiber reinforced epoxy resin.

15. The ultrasonic viscometer of claim 14, wherein said fiber reinforced epoxy resin further comprises a composite structural component.

16. A high temperature ultrasonic viscometer capable of measuring the cure state of a thermally curing composite at high temperature which comprises:

a piezoelectric element capable of sustaining high temperature without depolarization of cracking a first copper buffer rod welded to said piezoelectric element with a tin-silver solder; and a second copper-electroplated aluminum buffer rod welded to said first buffer rod with a tin-silver solder, said second buffer rod being shorter than said first buffer rod and adapted to be contacted with the thermally curing composite, whereby ultrasonic shear waves generated by said piezoelectric element are partially reflected at the interface of the two buffers to form a first echo, and the shear waves transmitted across said buffer-buffer interface are reflected at the interface of the second buffer and said composite to form a second echo, permitting said first and second echoes to be digitized and processed to obtain the complex reflection coefficient at the interface of said second buffer and said composite, from which the viscosity of the composite can be calculated and the cure state of the composite determined.

17. The ultrasonic viscometer of claim 16, wherein said piezoelectric element further comprises lithium niobate crystals and said piezoelectric element is gold-plated.

* * * * *